(12) United States Patent
Hitchcock et al.

(10) Patent No.: US 7,465,830 B2
(45) Date of Patent: Dec. 16, 2008

(54) METHOD OF PREPARING PSEUDONOREPHEDRINE

(75) Inventors: Shawn R. Hitchcock, Normal, IL (US); Jonathan Andrew Groeper, Bloomington, IL (US)

(73) Assignee: Illinois State University, Normal, IL (US)

( * ) Notice: Subject to any disclaimer, the term of this patent is extended or adjusted under 35 U.S.C. 154(b) by 0 days.

(21) Appl. No.: 11/836,510

(22) Filed: Aug. 9, 2007

(65) Prior Publication Data

US 2008/0058551 A1 Mar. 6, 2008

Related U.S. Application Data

(60) Provisional application No. 60/823,867, filed on Aug. 29, 2006.

(51) Int. Cl.
*C07C 215/20* (2006.01)
(52) U.S. Cl. .................................................. 564/355
(58) Field of Classification Search ........................ None
See application file for complete search history.

(56) References Cited

OTHER PUBLICATIONS

Grunewald J. Med. Chem 1988, 31, 1984-1986.*
Groeper et al : Tetrahedron: Asymmetry 17 (2006) 2884-2889.*
Buckley et al J. Am Chem Soc. 1981, 103, 6157-6163.*
Katz et al: Tetrahedron Letters 43, (2002) 557-559.*
Agami et al., "Chiral Oxazolidinones from N-Boc Derivatives of β-Amino Alcohols. Effect of a N-Methyl Substituent on Reactivity and Stereoselectivity," *Tetrahedron Lett.*, 34 (28), 4509-4512 (1993).
Ager et al., "1,2- Amino Alcohols and Their Heterocyclic Derivatives as Chiral Auxiliaries in Asymmetric Synthesis," *Chemical Reviews*, 96, 835-875 (1996).
Alles et al., "Chemical Pharmacology of *Catha edulis*," *J. Med. Chem.*, 3 (2), 323-352 (1961).
Boerner et al., "A Convenient Synthesis of Optically Pure (S,S)-Norpseudoephedrine," *Tetrahedron Lett.*, 30(8), 929-930 (1989).
Claremon et al., "Organolithium Addition to Aldehyde Dimethylhydrazones: A Highly Diasterocontrolled Syntehsis of Threo 2-Amino Alcohols and (1R,2R)-(-)-Norpseudoephedrine," *J. Am. Chem. Soc*, 108, 8265-8266 (1986).
Davies et al., "Base Induced C-5 Epimerisation of 4-Methyl-5-phenyl Oxazolidinones: Chiral Auxilliaries Derived from Norephedrine and Norpseudoephedrine," *Tetrahedron: Asym.*, 4(12), 2513-2516 (1993).
Emboden, Jr., W.A. *Narcotic Plants*, The Macmillan Company, New York, NY, 90-91 (1972).
Grue- Sørenson et al., "Biosynthesis of Ephedrine," *J. Am. Chem. Soc.* 110, 3714-3715 (1988).
Hwang, "Efficient Syntehsis of Ephedra Alcaloid Analogues Using an Enantiomerically Pure N-[(R)-(+)-α-Methylbenzyl]aziridine-2-carboxaldehyde," *J. Org. Chem.*, 61, 6183-6188 (1996).
Kim et al., "A New Approach to the Synthesis of Optically Active Norephedrine, Norpseudoephedrine and Cathinone via Double Asymmetric Induction," *Bull. Korean Chem. Soc.*, 24(11), 1641-1648 (2003).
Kreutz et al., "Baker's yeast reduction of (E)-1-phenyl-1,2-propanedione 2-(O-methyloxime). A key step for a (-)-norephedrine synthesis," *Tetrahedron: Asymm.*, 8(15), 2649-2653 (1997).
Martin et al., "Kinetic Resolution of Racemic Allylic Alcohols by Enantioselective Epoxidation. A Route to Substance of Absolute Enantiomeric Purity?" *J. Am. Chem. Soc.*, 103, 6237-6240 (1981).
Reddy et al., "An enantioselective synthesis of (1S,2S)-pseudoephedrive," *Tetrahedron Lett.*, 41, 953-954 (2000).
"Designating the Configuration of Stereogenic Centers," website address: http://www.sigmaaldrich.com/catalog/search/ProductDetail/SIGMA/C222 (printed on Aug. 15, 2006).

* cited by examiner

*Primary Examiner*—Samuel A Barts
(74) *Attorney, Agent, or Firm*—Drinker Biddle & Reath LLP

(57) ABSTRACT

A method of making high diastereoselective and enantiomerically pure pseudonorephedrine and the hitherto unknown compound (1R,2R) pseudonorephedrine.

22 Claims, 2 Drawing Sheets

METHOD OF PREPARING PSEUDONOREPHEDRINE

TECHNICAL FIELD OF THE INVENTION

This invention relates to the manufacture of pseudonorephedrine and, more particularly, to an efficient process for converting (1R,2S) norephedrine and (1S,2R)-norephedrine into (1S,2S)-pseudonorephedrine and into (1R,2R)-pseudonorephedrine and to the previously unknown (1R,2R)-pseudonorephedrine compound produced.

BACKGROUND OF THE INVENTION

*Ephedra* alkaloids are important as building blocks for chiral auxiliaries in asymmetric syntheses and catalytic asymmetric syntheses. Many of these amino alcohol derivatives also have medicinal properties. *Ephedra* alkaloids as extracted from the *Ephedra vulgaris* family contain two physiologically active compounds, ephedrine and pseudoephedrine. The natural mechanism by which pseudonorephedrine is produced is complex and largely unknown. The availability of pseudonorephedrine from commercial sources is limited as it is a component obtained from the extraction of the khat shrub (*Catha edilis*) found in eastern Africa (e.g., Ethiopia) and Saudi Arabia. See Sørenson, G. G.; Spenser, I. D.; *J. Am. Chem. Soc.* 1988, 110, 3714-3715. Only (1S,2S) pseudonorephedrine is produced naturally; (1R,2R)-pseudonorephedrine is unknown in nature or from commercial sources. See Alles, G. A.; Fairchild, M. D.; Jensen, M. *J Med. Chem.* 1961, 3, 323 and Emboden, Jr., W. A. *Narcotic Plants* 1972, The Macmillan Company, New York, N.Y. Furthermore, (1S,2S) pseudonorephedrine is produced in nature in such small quantities and is so difficult to synthesize commercially that currently the cost of one gram is nearly $20,000 and therefore its use is generally cost-prohibitive in both small large scale synthetic applications. Finally, the currently available methods for manufacturing pseudonorephedrine stereoisomers provide less than ideal results and generally call for potentially dangerous reagents and time-consuming processes.

Chemical synthesis of pseudonorephedrine, (also known as norpseudoephedrine or cathine), has been accomplished in the past with varying degrees of success using a variety of methods. Most of these reported methods afford at best moderate diastereoselectivities and also require the use of chromatography, relatively expensive reagents, halogenated solvents, or excessive time to perform. Also, reported methods lack the scalability necessary to produce this product on a commercial scale.

Nevertheless, there is a broad range of interest for the use of the *Ephedra* alkaloids in the synthetic organic chemistry community. Among the principal uses of the *Ephedra* alkaloids is in chiral templates. These chiral templates can either be stoichiometric or catalytic in their use. The development of organic catalysts like *Ephedra* alkaloids has become very important as both research groups in academia and industrial companies become interested in using smaller amounts of material repeatedly. Ultimately, this is environmentally beneficial. Catalytic processes are widespread in organic chemistry and thus the use of *Ephedra* alkaloids as catalysts is widespread as well.

The *Ephedra* alkaloids possess a wide variety of biological properties that have been of interest to medicinal community. See, for example, Ager, D. J.; Prakash, I.; Schaad, D. R. 1,2-*Amino Alcohols and Their Heterocyclic Derivatives as Chiral Auxiliaries in Asymmetric Synthesis. Chemical Reviews* (Washington, D.C.) 1966, 96, 835; and Andraws, R.; Chawla, P.; Brown, D. L. *Cardiovascular effects of ephedra alkaloids: a comprehensive review. Progress in Cardiovascular Diseases* 2005, 47, 217-225. While ephedrine and pseudoephedrine have been extensively studied, the reaction mechanisms and applications of norpseudoephedrine (pseudonorephedrine) are relatively unknown. The present invention provides an excellent opportunity for scientists to fill this void and to focus particularly on the pseudonorephedrine isomers.

One report of a "convenient" synthesis of pseudonorephedrine involved the conversion of an exotic chloramphenicol through a series of seven steps and purification by chromatography to afford an overall yield of 26% where the diastereoselectivity of the product was not addressed and therefore the extent of stereochemical purity is unknown. See Boerner, A.; Krause, A.; *Tetrahedron Lett.* 1989, 108(8), 929-930. Organometallics have also been used to convert enantiomerically enriched aziridines to their corresponding alkaloids. See Hwang, G.-I.; Chung, J.-H.; Lee, W. K. *J. Org. Chem.* 1996, 61, 6183-6188. Others have carried out the addition of methyllithium to a chiral, non-racemic α-substituted hydrazone to prepare pseudonorephedrine. See Claremon, D. A.; Lumma, P. K.; Phillips, B. T.; *J. Am. Chem. Soc.* 1986, 108, 8265-8266; and Martin, V. S.; Woodard, S. S.; Katsuki, T.; Yamada, Y.; Ikeda, M.; Sharpless, K. B. J., *J. Am. Chem. Soc.* 1981, 103, 6237-6240. The latter method involved multiple steps as well as a kinetic resolution protocol. Cho and coworkers carried out the asymmetric reduction of racemic β-propiophenones using borane reducing agents. See Kim, D. J.; Cho, B. T. *Bull. Korean Chem. Soc.* 2003, 24, 1641-1648. This method afforded moderate yields and poor diastereoselectivity as well as poor enantiomeric ratios. Reddy and coworkers devised methods that utilized Grignard reagents and paraformaldehyde for reduction of an L-alanine oxazolidinone to afford an inseparable mixture of 95:5 diastereomers favoring the pseudonorephedrine diastereomer. See Reddy, G. V.; Rao, G. V.; Sreevani, V.; Iyengar, D. S. *Tetrahedron Lett.* 2000, 41, 953-954.

Certain studies have afforded moderate to good diastereoselectivity in the pseudonorephedrine synthesized. The use of Baker's yeast by Moran and coworkers for the preparation of pseudonorephedrine involved enzymatic reduction of an α-keto-O-methyloxime and an impractical 120 hour reaction time. Moran and coworkers reported two different approaches in addition to this, the first included a process involving refluxing THF over LiAlH$_4$ for 24 hours to reduce an O-methyloxime to the product with only a diastereoselectivity of 4:1 (anti:syn). In the other approach, 30 g of sucrose and 30 g of Baker's yeast were required to convert 0.53 g of O-methyloxime into 0.28 g of product. See Kreutz, O. C.; Moran, P. J. S.; Rodriguez, J. A. R. *Tetrahedron: Asymm.* 1997, 8, 2649-2653. Other studies conducted by Agami and coworkers utilized intramolecular inversion of the C$_5$ portion of an oxazolidinone to achieve a 4:1 selectivity. See Agami, C.; Couty, F.; Hamon, L.; Venier, O.; *Tetrahedron Lett.*, 1993, 34(28), 4509-4512. The most efficient reported synthesis of pseudonorephedrine was by Davies and coworkers. It involved the epimerization of either a syn or anti oxazolidinone derived from norephedrine or pseudonorephedrine. See Davies, S. G.; Doisneau, G. J.-M.; *Tetrahedron: Asym.,* 1993, 4(12), 2513-2516. The Davies process used an oxazolidinone that was epimerized with n-butyllithium to afford a 4:1 ratio of anti:syn diastereomers. The best synthetic routes afforded 80% anti diastereoselectivity which is the best selectivity reported in literature where isomers could be separated known to the present inventors.

Due to the difficulties in manufacturing pseudonorephedrine, this compound is prohibitively expensive and not widely available. Enantiomerically enriched (S,S)-pseudonorephedrine from natural sources is even more expensive and difficult to obtain. See http://www.sigmaaldrich.com/catalog/search/ProductDetail/SIGMA/C222. To our knowledge, the (1R,2R)-pseudonorephedrine enantiomer is not even available from U.S. commercial sources.

The lack of an efficient process for synthesizing pseudonorephedrine enantiomers likely has hindered important research into the effects and possible uses of these compounds. If a process were available that would afford the enantiomers (1S,2S)-pseudonorephedrine and the previously unknown (1R,2R)-pseudonorephedrine in substantial amounts with minimal time and expense while simultaneously affording high diastereoselectivity and enantiomeric purity of the product, an important contribution to the art would be at hand.

The present invention is therefore directed to a new process that allows the formation of (1S,2S)-pseudonorephedrine and (1R,2R)-pseudonorephedrine from norephedrine starting materials in high diastereomeric purity and good overall yield by a process that is inexpensive, expedient, and readily scalable.

SUMMARY OF THE INVENTION

In accordance with the present invention, as illustrated in FIG. 1, the conversion of (1R,2S) norephedrine 1a into (1S,2S)-pseudonorephedrine 2a is achieved at enantiomeric purity levels of up to 99% ee beginning with acylation, preferably with di-tert-butyl dicarbonate and triethylamine, to afford the protected secondary carbamate derivative 3a. Upon the exposure of derivative 3a to additional triethylamine and methanesulfonyl chloride (or other appropriate agent), the oxazolidinones 4a, 5a, are formed, inducing the desired inversion of the phenyl group (FIG. 2). It is believed that the formation of the oxazolidinones is accomplished through the formation of a mesylated intermediate 4a, although this compound was not isolated nor was it observed in the crude product, and the invention is not intended to be limited to a reaction in which such an intermediate is formed. The formation of (1S,2S) pseudonorephedrine is completed through the hydrolysis of 5a preferably in a LiOH/H$_2$O solution as reflected in FIG. 3.

(1R,2R)-pseudonorephedrine can be synthesized in accordance with the present invention (as shown in FIGS. 5 and 6) using (1S,2R)-norephedrine 1b as the starting material. In the case of both (1S,2S)-pseudonorephedrine and (1R,2R)-pseudonorephedrine the synthesis is the result of the inversion of the stereochemistry at the benzyllic carbon of norephedrine via nucleophillic cyclization and the hydrolysis of an oxazolidinone intermediate.

BRIEF DESCRIPTION OF THE FIGURES

The following is a description of the Figures that are discussed below.

DESCRIPTION OF THE PREFERRED EMBODIMENTS

Figure 1:
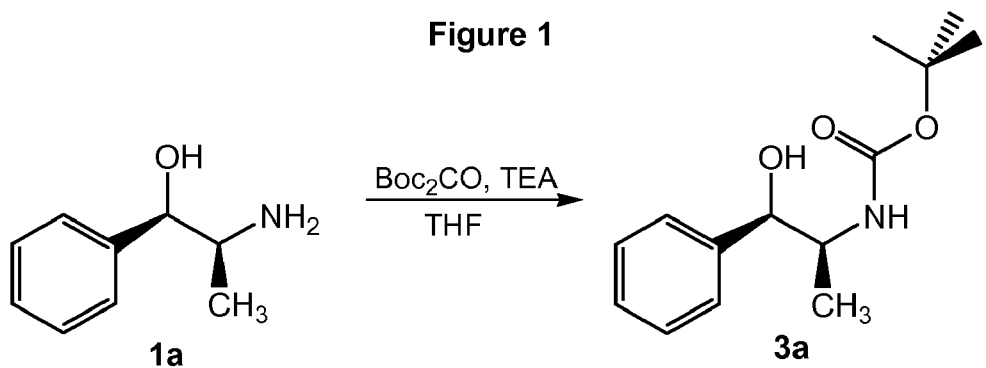
FIGS. 1-3 represent the synthesis of (1S,2S)-pseudonorephedrine.
Figure 2:
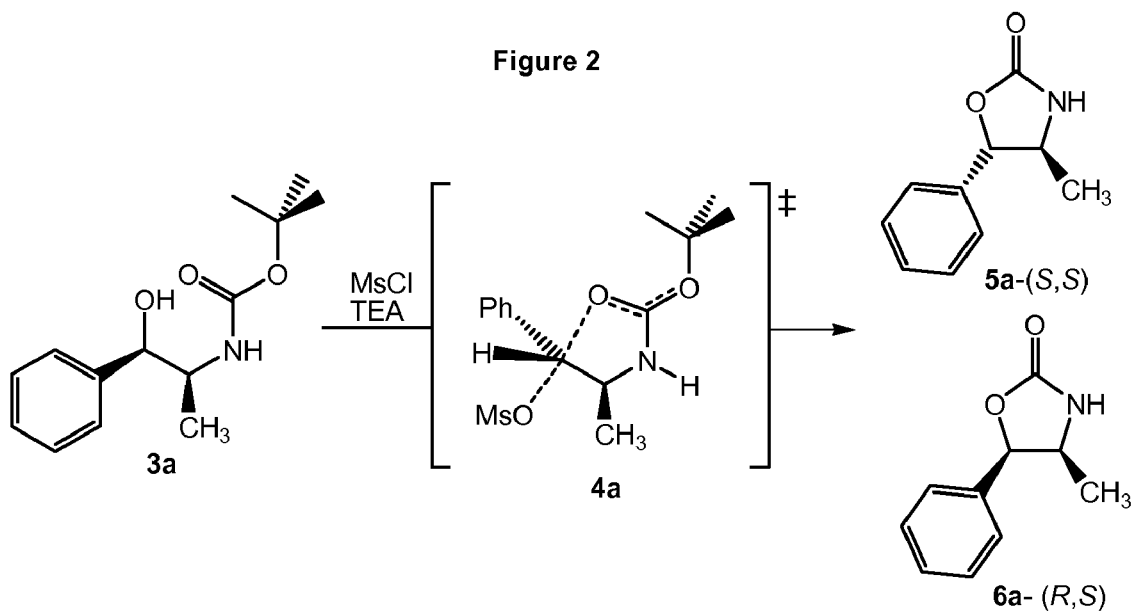
Figure 3:
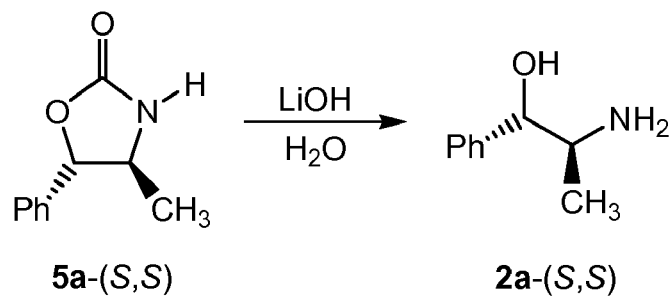
Figure 4:
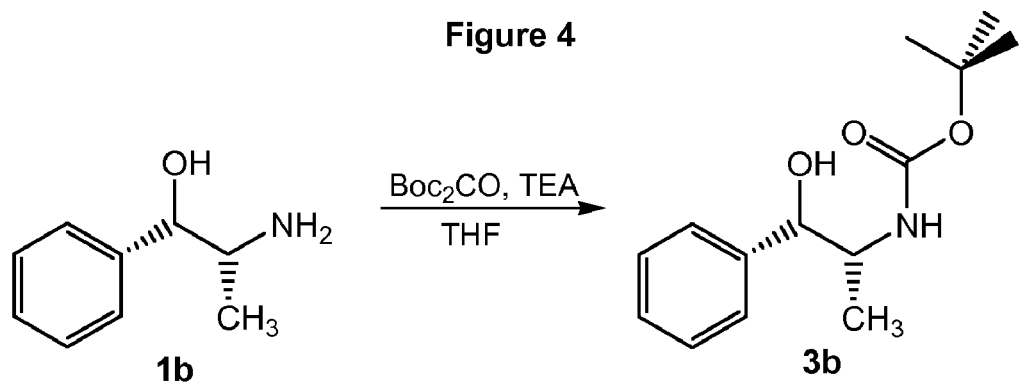
FIGS. 4-6 represent the synthesis of (1R,2R)-pseudonorephedrine.
Figure 5:
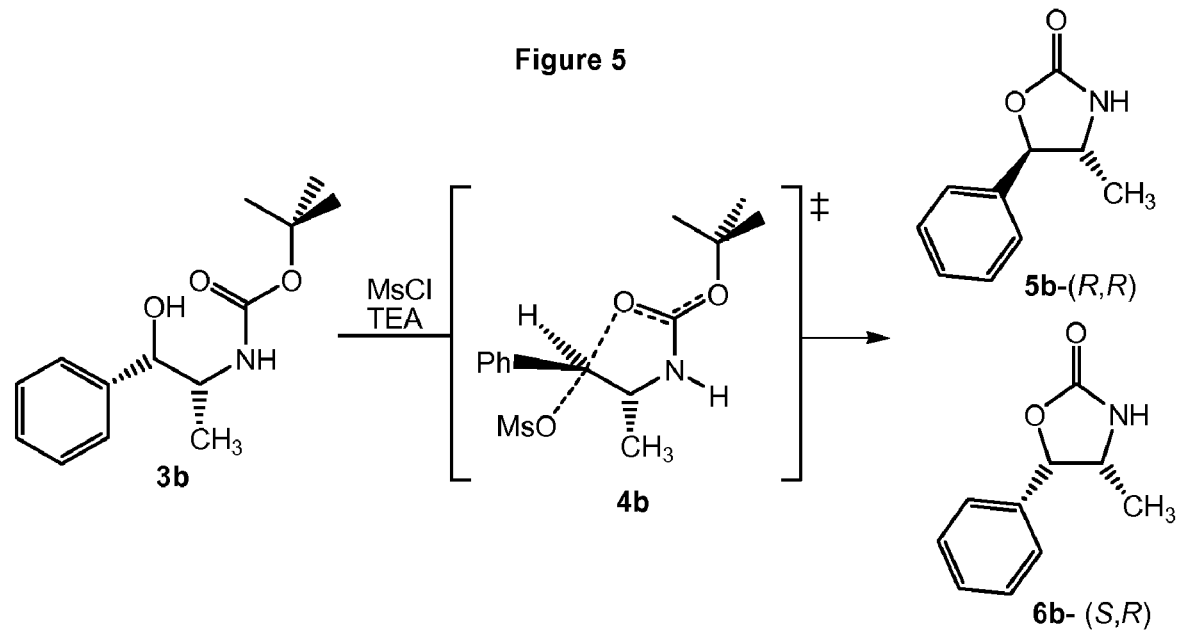
Figure 6:
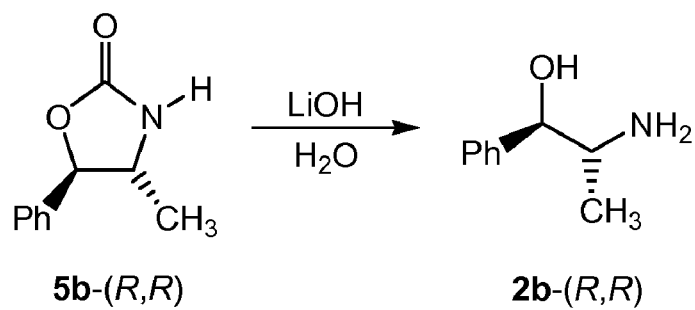

While the description below focuses on the formation of (1S,2S)-pseudonorephedrine as illustrated by the reactions of FIGS. 1-3, (1R,2R)-pseudonorephedrine may be prepared by the identical process using (1S,2R)-norephedrine as the starting material (FIGS. 4-6). Thus, as illustrated in FIG. 1, the conversion of (1R,2S) norephedrine 1a is achieved by acylation with di-tert-butyl dicarbonate and triethylamine to afford the protected secondary carbamate derivative 3a. Upon the exposure of 3a to additional triethylamine and methanesulfonyl chloride, the oxazolidinones 5a, 6a, are formed, inducing the desired inversion on the phenyl substituent leading to the target oxazolidinone 5a. An appropriate substitute for methanesulfonyl chloride may be used provided that, like methanesulfonyl chloride, acylation of the amine occurs as well as displacement of the alcohol, as discussed below.

It is believed that the formation of the oxazolidinone is accomplished through the formation of a mesylated intermediate 4a, although this compound was not isolated nor was it observed in the crude product. The invention is not intended to be limited to a reaction forming such an intermediate.

Typical reaction parameters are set forth in Table I below:

TABLE I

Reaction Parameters

| Entry | Solvent | Time 1(hrs) | Time 2(hrs) | Temp 2[a] | % Yield | d.r.[b] |
|---|---|---|---|---|---|---|
| 1 | CH$_2$Cl$_2$ | 2 | 3 | 40 | 82 | N/A |
| 2 | CH$_2$Cl$_2$ | 2 | 2 | 40 | 55 | 95:5 |
| 3 | CH$_2$Cl$_2$ | 2 | 16 | 25 | 70 | 95:5 |
| 4 | THF | 2 | 2.5 | 47 | 89 | 97:3 |
| 5 | THF | 2 | 3 | 49 | 90 | 99:1 |
| 6 | THF | 2 | 3 | 48 | 84 | 99:1 |

[a]Temperatures are in Celsius;
[b]HPLC data was gathered on a Shimadzu SCL-10 AVP system (d.r. are reported as anti:syn);
[c]Crude d.r. determined by HPLC on a Dynamax-100 Å column; and
[d]Crude d.r. determined by chiral HPLC on a Chiracel-OD column.

The reliability of the formation of pseudonorephedrine based oxazolidinone 5a, without the contamination of the diastereomeric norephedrine based oxazolidinone 6a was determined by subsequent HPLC studies that showed 5a the dominant isomer in each reaction. Table 1 illustrates the determined diastereoselectivities afforded in the process. Formation of pseudonorephedrine based oxazolidinone 5a was accomplished in both dichloromethane and THF solvent systems in good yield as well as high diastereoselectivity. Table I above illustrates the overall reaction in the formation of the oxazolidinone and also shows reaction conditions and results.

The formation of 5a (and 5b in FIG. 5) does not significantly deviate in either CH$_2$Cl$_2$ or THF in terms of yield and diastereoselectivity. If the synthesis is carried out in THF, the solution preferably will be heated to between about 45-50° C. for three hours of heating. If methylene chloride is used at a reflux temperature of about 45-50° C., about 2-3 hours of refluxing will be required to complete the cyclizing reaction whereas about 16 hours will be required at room temperature. Either solvent affords minimal diastereomeric scrambling.

Isolation of the oxazolidinone product is also intrinsically simple if desired although this step is not required in this process to produce 2a or 2b. In fact, any polar organic solvent can be used for trituration or the polar solvent may be exposed to a non-polar solvent (e.g, hexane) to recrystallize the oxazolidinone. Other known purification techniques can, of course, be used. Cyclization attempts with norephedrine and either p-toluenesulfonyl chloride or triflic anhydride were unsuccessful in both THF and methylene chloride perhaps due to steric interference in the case of tosyl chloride and the reaction is destroyed from triflic anhydride by the formation of the highly reactive trifluorosulfonic acid that reacts aggressively with the solvent and substrate, destroying both the solvent (THF) as well as the reactants.

The formation of pseudonorephedrine is completed through the hydrolysis of 5a (or 5b in FIG. 3) with water and a base such as LiOH, NaOH, KOH, Ca(OH)$_2$, or Mg(OH)$_2$ so long as the base is strong enough to open the oxazolidinone ring and the metal does not adversely interact with the end product. For example, the hydrolysis may be accomplished in a LiOH/H$_2$O solution with heating. Attempts at hydrolysis with Cs$_2$CO$_3$ and K$_2$CO$_3$ proved unsuccessful possibly because of the lower pKa of carbonate possibly not being strong enough to hydrolyze the oxazolidinone. Table II below illustrates the results of the hydrolytic cleavage of the oxazolidinone.

TABLE II

Hydrolytic Cleavage Of The Oxazolidinone

| Entry | Base % | Time (min) | Temp.[a] | % Yield |
|---|---|---|---|---|
| 1 | 10 | 30 | 80 | 82 |
| 2 | 10 | 45 | 90 | 91 |
| 3 | 5 | 30 | 85 | 94 |

[a]Temperatures are in Celsius

The ability of the end product to withstand the hydrolytic cleavage and maintain the overall configuration was supported by the X-ray crystallographic structure of (1S,2S)-pseudonorephedrine (CCDC No. 617758). The desired anti configuration of the chiral centers were determined to be present at the C1 and C2 positions, thus showing the successful inversion of the phenyl substituent at the C1 position.

The reactions of FIG. 1 (or FIG. 4) can be combined with the reaction in FIGS. 2 and 3 (or FIGS. 5 and 6) into a one step process to afford the pseudonorephedrine 2a (2b in FIG. 6) without having to stop at the end of each reaction, extract the product, purify and continue with the next reaction. One solvent that can be used for such a one-pot synthesis is THF. THF is preferred because of its good miscibility with water. Other organic solvents can of course be used.

The success of the total conversion of norephedrine to pseudonorephedrine relies on the hydrolysis of the oxazolidinone. It is preferred that this reaction be carried out at least about 80° C. and preferably at least 85° C. to 90° C. The reaction temperature should not exceed about 100° C. Generally, the organic solvent will have to be removed in order for the thermal requirement to be met. One efficient way to remove the THF is under aspirator vacuum while immersing the entire reactor vessel in a water bath at 60° C. to prevent the reactor from chilling and inhibiting the extraction of THF (or other polar organic solvent.).

After the THF is removed, the reaction may be heated to the appropriate temperature for example via replacement of the water jacket with a heating mantle. For example, the temperature can initially be taken to 80° C. in a single reaction hydrolysis of 5a (or 5b) and then increased to between 85° C. and 90° C. to purge as much butanol and TEA as possible to minimize impurities that could be troublesome in the extraction process and require additional purification. To encourage the butanol and TEA to escape, the hydrolyses may be performed without the aid of a condenser in open air. The varied temperatures do not yield any compromising stereochemical scrambling that can be seen by $^1$H-NMR spectroscopy so it is assumed that the diastereoselectivity gained in the nucleophilic inversion confirmed by HPLC for 5a (or 5b) was maintained. The diastereoselectivity is not compromised through this one-pot synthesis and the results are comparable as if each of the three reactions had been performed alone.

The one-pot syntheses have thus far yielded between 55-60% products, thus indicating an average yield of 80-85% for each of the three steps. This is keeping in line with the conversion as if it had been performed in three separate steps except that which takes three steps individually may now be accomplished in one step, thereby saving the setup and extraction time of three separate reactions and extractions.

This one-pot synthesis provides the pseudonorephedrine in high diastereoselectivity and good yield. This new method produces either isomer of norpseudoephedrine in a manner superior to any currently available in the literature.

Preferred times and temperatures for the practice of the invention are set for the Table III below:

TABLE III

Preferred Times and Temperatures

| | Solvent[a] | Acylation | | Cyclization | | Vacuum | | Hydrolysis | |
| | | Temperature[b] | Time | Temperature[b] | Time | Temperature[b] | Time | Temperature[b] | Time |
|---|---|---|---|---|---|---|---|---|---|
| One-pot synthesis | THF | rt-65 | 1-3 hours[d,e] | rt-65 | 1-16 hours | 40-60 | 10-60 min. | rt-100 | 15-180 min. |
| Oxazolidinone Synthesis | THF | rt-65 | 1-3 hours | rt-65 | 1-16 hours | NA | NA | NA | NA |
| | CH$_2$Cl$_2$ | rt-40 | 1-3 hours | rt-40 | 1-16 hours | NA | NA | NA | NA |
| Two-step Process | THF | rt-65 | 1-3 hours | rt-65 | 1-16 hours | NA | NA | rt-100 | 15-180 min. |
| | CH$_2$Cl$_2$ | rt-40 | 1-3 hours | rt-40 | 1-16 hours | NA | NA | rt-100 | 15-180 min. |

[a]Any organic solvent will suffice although reaction times may vary; these are examples of solvents that may be used.
[b]Temperatures are in Celsius.
[c]Preferred upper limit will be just below boiling point of solvent and temperature at which deacylation will occur.
[d]At room temperatures, using THF.
[e]Time will depend on temperature and solvent and can be determined by thin layer chromatographic analysis of the progress of the reaction.

The following examples describe embodiments of the present invention and should not be construed as limiting its scope in any way.

EXAMPLES

1. Enantiomerically enriched (1R,2S) norephedrine (99%) and (1S,2R) norephedrine (98%) were purchased from Sigma-Aldrich. All reaction vessels were flame dried under an inert nitrogen atmosphere. Tetrahydrofuran (THF) was distilled over lithium aluminum hydride and triethylamine was distilled over calcium hydride. All extractions were dried over anhydrous magnesium sulfate, gravity filtered, and the solvents removed via rotary evaporation.

General Procedure for One-Pot Synthesis of Pseudonorephedrine

THF was distilled directly into a 2 L three-neck reaction vessel fitted with an addition funnel and thermometer through a Claisen adapter. To this was added the appropriate (1R,2S)-norephedrine to provide a 0.3 M solution. Triethylamine (1.1 eq) was added via syringe through the Claisen adapter septum to the solution and an ice bath was added. (Note: positive pressure should be maintained although nitrogen flushing is not recommended.) After sufficient cooling, di-tert-butyl dicarbonate (1.05 eq) was added and the ice was removed after 5 minutes. The reaction was allowed to proceed at ambient temperature for two hours when the reaction was cooled to in another ice bath. An additional portion of TEA (1.1 eq) was added and then methanesulfonyl chloride (1.5 eq) was added dropwise through the addition funnel. The ice was removed after 5 minutes and the solution was heated to 45° C. for three hours to afford a light orange solution. An aqueous of 10% LiOH solution equal to the original volume of THF was prepared and added to the solution. The flask was fitted with a distillation arm, a condenser, take-off vacuum adapter, and a collection flask with the entire apparatus sealed with vacuum grease. The collection flask was also immersed in an ice/NaCl water bath. The main flask was immersed in a 60° C. water bath. A gentle vacuum was applied by a water aspirator for 30 minutes until the solvent was removed after which the vacuum apparatus and the water bath was removed and the heating mantle was replaced under the main vessel. The reaction was then heated to 80-90° C. The reaction was allowed to proceed in open air with no condenser for one hour at which time the heat was removed and the solution was allowed to cool. After the reaction has cooled, the water was acidified with 6 M HCl until the solution turned clear. The pH tested and adjusted to afford an approximate pH of 3-4. Extraction was performed by exposure of the water to a portion of chloroform (3×75 mL). The water was then basified with 6 M KOH until the pH was approximately 8. The water was then exposed to chloroform (6×75 mL) and the solvents removed. The resulting white solid formed and purification was performed with a combination of trituration and recrystallization in hexanes and ethyl acetate however this may not be necessary as the initial washes at pH 3-4 may remove impurities. Progress of the reaction may be monitored by TLC (1:1 ethyl acetate:hexanes). (Boc-norephedrine $R_f$≈0.64, Oxazolidinone $R_f$≈0.25).

2. In the hydrolysis method for the conversion, initially a 5% aqueous base solution was used. This resulted in loss of product due to the lack of excess base. When the water volume was reduced from a 1:1 ratio of water to THF by 50% and the base is increased in concentration to 10%, an excess molar amount of base is present for the hydrolysis. However, this proved to be an insufficient amount of base so it was increased to 15% LiOH to afford a 3:1 molar ratio of base to substrate while maintaining the 25% reduction in water to THF. However, this proved not as efficient as the reduction of water and the increase of base caused for the LiOH to not go completely into solution so the base percentage was decreased to 10 and the water to THF ratio was taken back to a 1:1 ratio. The upshot of this is that the level of base should be at least about 5 times the stoichiometric amount of norephedrine present and enough water should be present to ensure that a large excess of base present. In addition, upon completion of the hydrolysis, the solution may be acidified and the water exposed to chloroform to draw out any organic impurities. The extraction may be completed by making the solution just slightly basic (e.g., pH≈8) and extracting with chloroform to complete the process.

3. This identical procedure as described above may be carried out replacing the THF with methylene chloride, except that the cyclization will take place at ambient temperature over a 16 hour period or with heating for two hours to produce the oxazolidinone. Extraction is performed in the same manner as the THF procedure although the acid/base extraction is not necessary and the same product can be produced.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be

What we claim is:

1. A method of making (1S,2S) pseudonorephedrine comprising:
   A) providing (1R,2S) norephedrine as a starting material;
   B) acylating the amine to produce

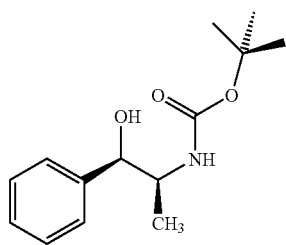

as a secondary carbamate derivative;
   C) treating the secondary carbamate derivative to displace the alcohol and invert the phenyl group to produce the oxazolidinones

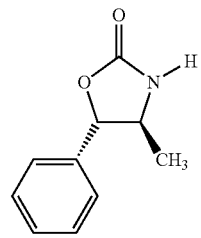

as a major product, and

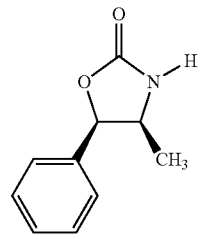

as a minor product; and

D) hydrolyzing the major product oxazolidinone to form (1S,2S) pseudonorephedrine.

2. The method of claim 1 in which the acylation is achieved by treating the norephedrine with di-tert-butyl dicarbonate and triethylamine.

3. The method of claim 1 in which the oxazolidinones are produced by treating the secondary carbamate derivative with triethylamine and methanesulfonyl chloride to displace the alcohol and invert the phenyl group.

4. The method of claim 3 in which the solution is refluxed in dichloromethane or tetrahydrofuran at a reflux temperature of about 45-50° C.

5. The method of claim 1 in which the major product oxazolidinone is purified by triturating in a polar organic solvent or by exposing the major product oxazolidinone polar solvent to a non-polar solvent to recrystalize the product.

6. The method of claim 1 in which the hydrolysis is carried out using a base strong enough to open the major product oxazolidinone in which the metal of the base does not adversely interact with the end product.

7. The method of claim 6 in which the base is chosen from the group consisting of LiOH, NaOH, KOH, Ca(OH)$_2$, and Mg(OH)$_2$.

8. The method of claim 1 in which the major product oxazolidinone is hydrolyzed in a LiOH/H$_2$O solution.

9. The method of claim 1 in which the hydrolysis is carried out at a temperature of about 80-100° C.

10. The method of claim 1 carried out as a one pot process in an organic solvent without stopping at the end of each reaction, extracting intermediate products, purifying and continuing with the next reaction.

11. The method of claim 10 in which any organic solvent is removed before the hydrolysis step while the solution is maintained at a temperature of about 60° C. and then the mixture is heated to a temperature of about 80-100° C.

12. A method of making (1R,2R) pseudonorephedrine comprising:
    A) providing (1S,2R) norephedrine as a starting material;
    B) acylating the amine to produce

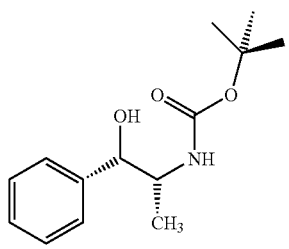

as a secondary carbamate derivative;

C) treating the secondary carbamate derivative to displace the alcohol and invert the phenyl group to produce the oxazolidinones

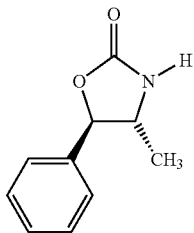

as a major product; and

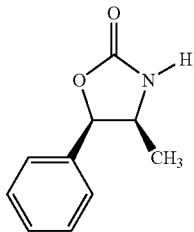

as a minor product; and
D) hydrolyzing the major product oxazolidinone to form (1R,2R) pseudonorephedrine.

13. The method of claim 12 in which the acylation is achieved by treating the norephedrine with di-tert-butyl dicarbonate and triethylamine.

14. The method of claim 12 in which the oxazolidinones are produced by treating the secondary carbamate derivative with triethylamine and methanesulfonyl chloride to displace the alcohol and invert the phenyl group.

15. The method of claim 14 in which the solution is refluxed in dichloromethane or tetrahydrofuran at a reflux temperature of about 45-50° C.

16. The method of claim 12 in which the major product oxazolidinone is purified by triturating in a polar organic solvent or by exposing the major product oxazolidinone polar solvent to a non-polar solvent to recrystalize the product.

17. The method of claim 12 in which the hydrolysis is carried out using a base strong enough to open the major product oxazolidinone in which the metal of the base does not adversely interact with the end product.

18. The method of claim 17 in which the base is chosen from the group consisting of LiOH, NaOH, KOH, Ca(OH)$_2$, and Mg(OH)$_2$.

19. The method of claim 12 in which the major product oxazolidinone is hydrolyzed in a LiOH/H$_2$O solution.

20. The method of claim 12 in which the hydrolysis is carried out at a temperature of about 80-100° C.

21. The method of claim 12 carried out as a one pot process in an organic solvent without stopping at the end of each reaction, extracting intermediate products, purifying and continuing with the next reaction.

22. The method of claim 21 in which any organic solvent is removed before the hydrolysis step while the solution is maintained at a temperature of about 60° C. and then the mixture is heated to a temperature of about 80-100° C.

* * * * *